(12) United States Patent
Skowerski et al.

(10) Patent No.: US 9,328,132 B2
(45) Date of Patent: May 3, 2016

(54) RUTHENIUM COMPLEXES, THEIR USE IN THE METATHESIS REACTIONS, AND A PROCESS FOR CARRYING OUT THE METATHESIS REACTION

(71) Applicant: Apeiron Synthesis S. A., Wroclaw (PL)

(72) Inventors: Krzysztof Skowerski, Jablonowo Pomorskie (PL); Michal Bieniek, Wroclaw (PL)

(73) Assignee: APEIRON SYNTHESIS S.A., Wroclaw (PL)

( * ) Notice: Subject to any disclaimer, the term of this patent is extended or adjusted under 35 U.S.C. 154(b) by 0 days.

(21) Appl. No.: 14/406,741

(22) PCT Filed: Jul. 26, 2013

(86) PCT No.: PCT/EP2013/065839
§ 371 (c)(1),
(2) Date: Dec. 9, 2014

(87) PCT Pub. No.: WO2014/016422
PCT Pub. Date: Jan. 30, 2014

(65) Prior Publication Data
US 2015/0158896 A1 Jun. 11, 2015

(30) Foreign Application Priority Data
Jul. 27, 2012 (PL) .......................................... 400162

(51) Int. Cl.
| | | |
|---|---|---|
| *C07F 15/00* | (2006.01) | |
| *C08F 132/06* | (2006.01) | |
| *C07D 307/28* | (2006.01) | |
| *C07C 67/333* | (2006.01) | |
| *C07C 67/293* | (2006.01) | |
| *C07C 67/475* | (2006.01) | |
| *C08G 61/08* | (2006.01) | |

(52) U.S. Cl.
CPC ........... *C07F 15/0046* (2013.01); *C07C 67/293* (2013.01); *C07C 67/333* (2013.01); *C07C 67/475* (2013.01); *C07D 307/28* (2013.01); *C08F 132/06* (2013.01); *C07C 2101/10* (2013.01); *C08G 61/08* (2013.01); *C08G 2261/3325* (2013.01); *C08G 2261/418* (2013.01)

(58) Field of Classification Search
CPC .. C07C 67/293; C07C 67/333; C07C 67/475; C07C 2101/10; C07D 307/28; C07F 15/0046; C08F 132/06; C08G 2261/3325; C08G 2261/418; C08G 61/08
USPC ............. 526/308; 548/101; 549/507; 556/23; 560/122, 254; 546/2
See application file for complete search history.

(56) References Cited

U.S. PATENT DOCUMENTS

2003/0055262 A1* 3/2003 Grubbs ............... C07F 15/0046
548/103

FOREIGN PATENT DOCUMENTS

| PL | 199428 B1 | 9/2008 |
|---|---|---|
| WO | 2008/034552 A1 | 3/2008 |
| WO | 2010/127829 A1 | 11/2010 |
| WO | 2014/016422 A1 | 1/2014 |

OTHER PUBLICATIONS

Coalter et al. (Carbene transposition involving double dehydrogenation of an sp3 carbon, Chem. Commun., 2001, 1158-1159).*
Bishop et al., "Substituent dependence of the reactions of [RuCl$_2$(PPh$_3$)$_3$] with bulky aromatic thiols," *Dalton Trans.*10:1267-1270, 2006.
Coalter III et al., "Carbene transposition involving double dehydrogenation of an sp$^3$ carbon," *Chem. Commun.*:1158-1159, 2001.
Drozdzak et al., "Latent Olefin Metathesis Catalysts for Polymerization of Dcpd," *Macromol. Symp.* 293:1-4, 2010.
Grela et al., "A Highly Efficient Ruthenium Catalyst for Metathesis Reactions," *Agnew. Chem. Int.Ed.* 41(21):4038-4040, 2002.
International Preliminary Report on Patentability, mailed Oct. 23, 2014, for corresponding International Application No. PCT/EP2013/065839, 11 pages.
International Search Report and Written Opinion, mailed Sep. 30, 2013, for corresponding International Application No. PCT/EP2013/065839, 10 pages.

(Continued)

*Primary Examiner* — Ling Choi
*Assistant Examiner* — Chun-Cheng Wang
(74) *Attorney, Agent, or Firm* — Seed IP Law Group PLLC

(57) ABSTRACT

The invention is related to the metal complexes of the general formula (1). The invention is related also to the use of metal complexes of the formula 1 as (pre)catalysts for the olefin metathesis reactions, as well as to the process for carrying out the olefin metathesis reaction.

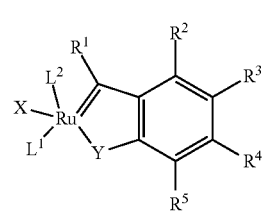

19 Claims, No Drawings

(56) References Cited

OTHER PUBLICATIONS

Kozłowska et al., "Chelating Ruthenium Phenolate Complexes: Synthesis, General Catalytic Activity, and Applications in Olefin Metathesis Polymerization," *Chem. Eur. J.* 20:14120-14125, 2014.

Monsaert et al., "Latent olefin metathesis catalysts," *Chem. Soc. Rev.* 38:3360-3372, 2009.

Perring et al., "Assembly of Organic Monolayers on Polydicyclopentadiene," *Langmuir* 24:10480-10487, 2008.

Pietraszuk et al., "Ruthenium-Amido Complexes: Synthesis, Structure, and Catalytic Activity in Olefin Metathesis," *Chem. Eur. J.* 18:6465-6469, 2012.

Polish Office Action, dated Oct. 8, 2012, for corresponding Polish Application No. P.400162, 2 pages.

Vougioukalakis et al., "Ruthenium-Based Heterocyclic Carbene-Coordinated Olefin Metathesis Catalysts," *Chem. Rev.* 110:1746-1787, 2010.

Wierzbicka et al., "Molecules of ruthenium-based olefin metathesis catalysts as two- and three-photon absorbers," *Dalton Trans.* 41:13258-13260, 2012.

* cited by examiner

RUTHENIUM COMPLEXES, THEIR USE IN THE METATHESIS REACTIONS, AND A PROCESS FOR CARRYING OUT THE METATHESIS REACTION

The invention concerns novel metal complexes, their use as (pre)catalysts in the metathesis reaction as well as the process for carrying out the metathesis reaction.

The metathesis of olefins is an important tool in the organic synthesis (*Handbook of Metathesis*, Vol. I-III, Grubbs, R. H., ed.; Wiley-VCH, 2003).

Many ruthenium complexes actively catalysing the metathesis of olefins are well known in the art (see, the review: Vougioukalakis, G. C.; Grubbs, R. H. *Chem. Rev.* 2010, 110, 1746). The III-rd generation complexes (such as Gru-III, Ind-III) were shown to be highly useful (pre)catalysts of the ring-opening metathetic polymerisation (ROMP) reaction.

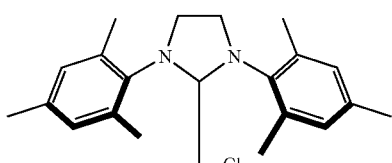

Gru III

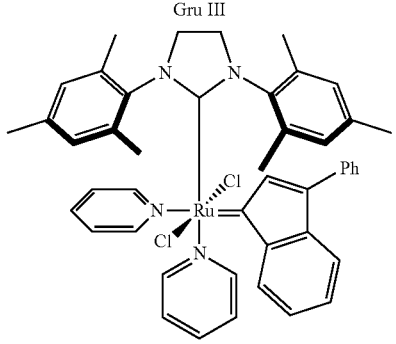

Ind III

The third-generation catalysts initiate the metathesis reactions very promptly, whereas, in some metathesis applications, such as mould ROMP polymerisation, it is preferred to use a (pre)catalyst that does not initiate the reaction immediately after adding it to the substrate but only after an appropriate initiation by chemical agents, temperature or light. The complexes characterised by delayed initiation are often termed "dormant catalysts" (Monsaert, S.; Vila, A. L.; Drozdzak, R.; Van Der Voort, P.; Verpoort, F., *Chem. Soc. Rev.*, 2009, 38, 3360; R. Drozdzak, N. Nishioka, G. Recher, F. Verpoort, *Macromol. Symp.* 2010, 293, 1-4). Exemplary "dormant catalysts" are the complexes A-F, as well as the recently obtained P-1 and P-2 (Pietraszuk, C.; Rogalski, S.; Powala, B.; Miętkiewski, M.; Kubicki, M.; Spólnik, G.; Danikiewicz, W.; Woźniak, K.; Pazio, A.; Szadkowska, A.; Kozlowska, A.; Grela, K., *Chem. Eur. J,* 2012, 18, 6465-6469).

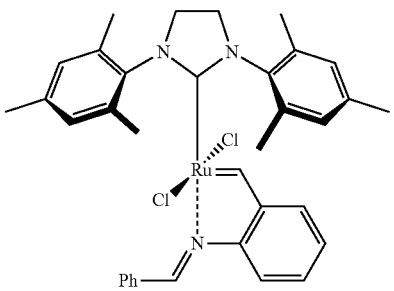

A

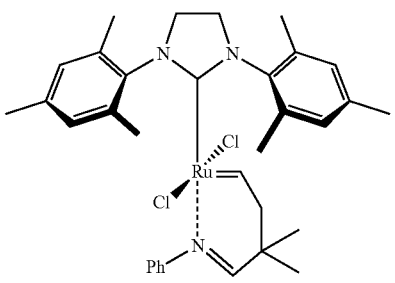

B

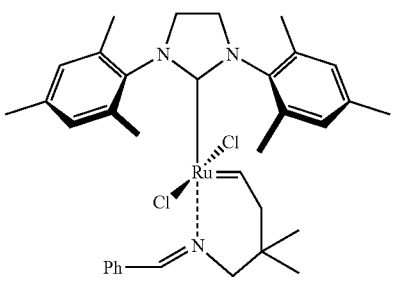

C

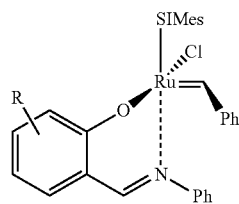

D

D'

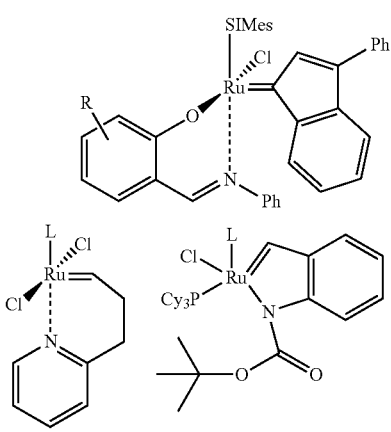

E [L = PCy3]
F [L = SIMes]

P-1 [L = PCy3]
P-2 [L = SIMes]

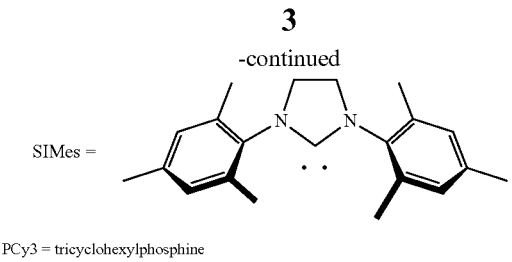

PCy3 = tricyclohexylphosphine

The mould ROMP polymerisation allows obtaining finished articles. Dicyclopentadiene is one of the monomers frequently used for the mould polymerisation. Polydicyclopentadiene, being obtained by polymerisation of dicyclopentadiene, features, inter alia, a low moisture absorption as well as resistance to stress and high temperature. This is why parts of vehicles and specialised containers for the chemical industry are more and more frequently manufactured by the (mould) ROMP polymerisation of dicyclopentadiene.

From the viewpoint of practical industrial applications, it is of extreme importance that the (pre)catalysts are stable in the presence of oxygen as well as moisture, during both their synthesis and purification, and also during their use in the metathesis reaction. Development of stable and active (pre) catalysts for metathesis of olefins (such as G, H and I) allowed to broaden significantly the scope of possible uses of this transformation. Nevertheless, these complexes are still prepared and used in metathesis reactions in atmosphere of inert gas, in dry solvents, since their stability against oxygen and moisture is limited.

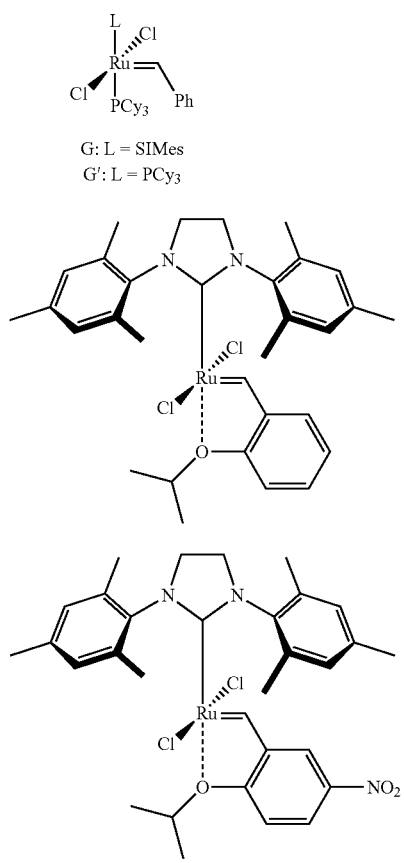

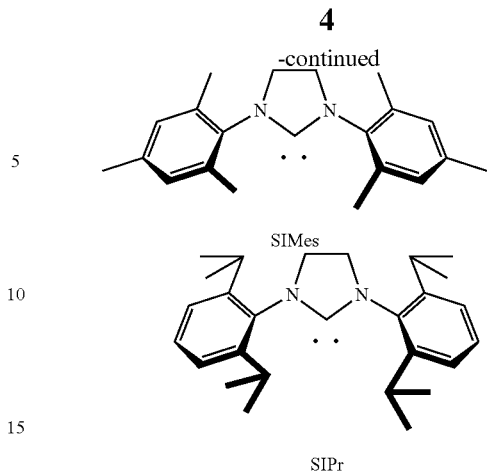

It was observed that the ruthenium complexes depicted by the formula 1:

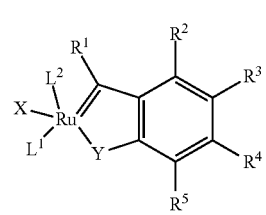

possessing in their structure a covalent metal-oxygen or metal-sulphur bond were very stable and might be prepared without any protective atmosphere of inert gas, as well as in the solvents of analytical grade (pro analysi). Following their suitable activation, the complexes of the general formula 1 actively catalyse the metathesis reactions carried out in the presence of air. Moreover, the complexes of the general formula 1 actively catalyse the metathesis reactions only after being activated by chemical agents, and they are very hardly susceptible to thermal activation. These properties enable excellent control of the time of initiating the reaction; such a property is very useful especially for the ROMP-type reactions. It was unexpectedly observed that the complexes of the general formula 1 allowed obtaining polydicyclopentadiene via the ROMP-type reaction carried out in the air, the amount of the (pre)catalyst used being significantly lower than that in the case of using classical complexes. Even an amount of 100 ppm (parts per million, by weight) of the complex according to the invention, that contains an NHC ligand (an N-Heterocyclic Carbene ligand), effectively catalyses polymerisation of dicyclopentadiene (DCPD). This amount corresponds to the mole ratio of the monomer to the (pre)catalyst being of about 65,000:1. Thus, this amount of the (pre)catalyst is less than half of that in the case of the catalyst G (M. Perring, N. B. Bowden *Langmuir,* 2008, 24, 10480-10487). Also, the (pre)catalyst according to the invention containing two phosphine ligands is more active in the ROMP reaction of polydicyclopentadiene than the structurally similar complex G'. Besides, it was unexpectedly observed, that the effect of an electron-acceptor substituent on the rate of initiation of a (pre)catalyst was reversed in the case of complexes of the general formula 1 compared to the case of the classical complex of the Hoveyda-Grubbs type (K. Grela, S. Harutyunyan, A. Michrowska, *Angew. Chem. Int. Ed.* 2002, 41, No. 21).

The possibility of affecting the properties of a (pre)catalyst by changing its ligands and, in consequence, the possibility of optimal tuning its activity for a specific reaction, is extremely valuable. As a rule, a higher stability is observed for the catalysts containing an N-heterocyclic SIPr ligand in their structure, compared to the (pre)catalysts containing the SIMes ligand, although the differences in their effectiveness in the metathesis reactions are usually not very significant. Unexpectedly, it was found that the alteration of an N-heterocyclic carbene ligand (NHC) had a high effect on effectiveness of the complexes of the general formula 1 according to the invention. It was found that the catalyst 1 containing the NHC ligand, SIPr, effectively catalysed the reactions of ring-closing metathesis as well as the ene-yne type reaction, whereas it demonstrated lower activity both in the ROMP type reaction and CM (cross-metathesis) reaction. In turn, a catalyst of the general formula 1 containing the NHC ligand, SIMes, very effectively catalyses the CM reactions as well as the ROMP type reactions, whereas it demonstrates lower effectiveness in the ring-closing metathesis reaction.

The invention is related to the complexes of the general formula 1:

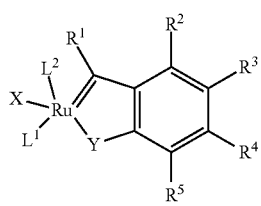

1 wherein,

X is an anionic ligand;

Y is oxygen or sulphur;

$L^1$ and $L^2$ represent independently a neutral ligand;

$R^1$ is hydrogen, $C_{1-20}$ alkyl, $C_{2-20}$ alkenyl, $C_{2-20}$ alkynyl or $C_{5-10}$ aryl;

$R^2$, $R^3$, $R^4$ and $R^5$ are independently hydrogen, halo, $C_1$-$C_{16}$ alkyl, $C_1$-$C_{16}$ alkoxy, $C_1$-$C_{16}$ perfluoroalkyl, $C_3$-$C_7$ cycloalkyl, $C_2$-$C_{16}$ alkenyl, $C_5$-$C_{14}$ aryl, $C_5$-$C_{14}$ perfluoroaryl, $C_3$-$C_{12}$ heterocyclyl, —$OR^6$, —$NO_2$, —COOH, —$COOR^6$, —$CONR^6R^7$, —$SO_2NR^6R^7$, —$SO_2R^6$, —CHO, —$COR^6$, wherein $R^6$ and $R^7$ are independently $C_1$-$C_6$ alkyl, $C_1$-$C_6$ perfluoroalkyl, $C_5$-$C_{14}$ aryl, $C_5$-$C_{14}$ perfluoroaryl; $R^2$, $R^3$, $R^4$ and $R^5$ may be optionally joined together to form a substituted or unsubstituted, fused carbocyclic ring $C_{4-8}$, or a substituted or unsubstituted, fused aromatic ring; provided that if X is chloro, Y is oxygen, $L^1$ is tricyclohexylphosphine, each of $R^1$, $R^2$, $R^3$ and $R^4$ is hydrogen, and $R^5$ is methyl, then $L^2$ is different from $L^1$.

The crystalline structure of the complex excluded by the above proviso from the scope of the invention has been already described by J. N. Coalter et al., Chem. Commun. 2001, 1158-1159.

Preferably, in the formula 1, the substituents $R^1$, $R^2$, $R^3$, $R^4$ and $R^5$ as well as Y are as defined above, and X is halo, —$OR^8$, —$O(C=O)R^8$, —$O(SO_2)R^8$, wherein $R^8$ is $C_1$-$C_{12}$ alkyl, $C_3$-$C_{12}$ cycloalkyl, $C_5$-$C_{14}$ aryl, that is optionally substituted with at least one of $C_1$-$C_6$ alkyl, $C_1$-$C_6$ perhaloalkyl, $C_1$-$C_6$ alkoxy or halo;

$L^1$ is of the formula $PR^9(R^{10})(R^{11})$, wherein $R^9$, $R^{10}$ and $R^{11}$ are independently $C_{1-12}$ alkyl, $C_{1-12}$ alkoxy, $C_{3-12}$ cycloalkyl, $C_{5-14}$ aryl, $C_{5-14}$ aryloxy, $C_{5-12}$ heterocyclyl; and two substituents from among $R^9$, $R^{10}$ and $R^{11}$ may additionally join together to form a cyclic system; or $L^1$ is an N-heterocyclic compound;

$L^2$ is an N-heterocyclic carbene ligand.

Preferably, in the formula 1, the substituents $R^1$, $R^2$, $R^3$, $R^4$ and $R^5$ as well as Y are as defined above, and X is halo, —$OR^8$, —$O(C=O)R^8$, —$O(SO_2)R^8$, wherein $R^8$ is $C_1$-$C_{12}$ alkyl, $C_3$-$C_{12}$ cycloalkyl, $C_5$-$C_{14}$ aryl, that is optionally substituted with at least one of $C_1$-$C_6$ alkyl, $C_1$-$C_6$ perhaloalkyl, $C_1$-$C_6$ alkoxy or halo;

$L^1$ and $L^2$ are independently of the formula $PR^9(R^{10})(R^{11})$, wherein $R^9$, $R^{10}$ and $R^{11}$ are independently $C_{1-12}$ alkyl, $C_{1-12}$ alkoxy, $C_{3-12}$ cycloalkyl, $C_{5-14}$ aryl, $C_{5-14}$ aryloxy, $C_{5-12}$ heterocyclyl; and two substituents from among $R^9$, $R^{10}$ and $R^{11}$ may additionally join together to form a cyclic system; or $L^1$ or $L^2$ are an N-heterocyclic compound selected from the group comprising: pyridine, 4-(N,N-dimethylamino)pyridine, 3-bromopyridine, piperidine, morpholine, pyridazine, pyrimidine, pyrazine, piperazine, 1,2,3-triazole, 1,3,4-triazole, 1,2,3-triazine as well as 1,2,4-triazine.

More preferably, in the formula 1,

X is chloro;

$R^1$ is hydrogen;

$R^2$, $R^3$, $R^4$ and $R^5$ are independently hydrogen or nitro;

Y is oxygen;

$L^1$ is tricyclohexylphosphine, triphenylphosphine, pyridine or 3-bromopyridine;

$L^2$ is a ligand of the formula 2a or 2b:

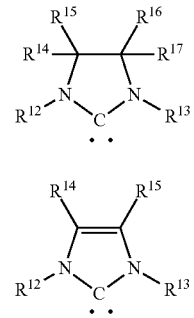

where:

$R^{12}$, $R^{13}$ are independently $C_1$-$C_{12}$ alkyl, $C_3$-$C_{12}$ cycloalkyl, $C_2$-$C_{12}$ alkenyl, $C_5$-$C_{14}$ aryl, optionally substituted with at least one of $C_1$-$C_6$ alkyl, $C_1$-$C_6$ perhaloalkyl, $C_1$-$C_6$ alkoxy or halo;

$R^{14}$, $R^{15}$, $R_{16}$, $R^{17}$ are independently hydrogen, $C_1$-$C_{12}$ alkyl, $C_3$-$C_{12}$ cycloalkyl, $C_2$-$C_{12}$ alkenyl, $C_5$-$C_{14}$ aryl, optionally substituted with at least one of $C_1$-$C_6$ alkyl, $C_1$-$C_6$ perhaloalkyl, $C_1$-$C_6$ alkoxy or halo, and $R^{14}$, $R^{15}$, $R^{16}$, $R^{17}$ may optionally join together to form a substituted or unsubstituted, fused carbocyclic ring $C_{4-8}$, or a substituted or unsubstituted, fused aromatic ring.

More preferably, in the formula 1,

X is chloro;

$R^1$ is hydrogen;

$R^2$, $R^3$, $R^4$ and $R^5$ are independently hydrogen or nitro;

Y is oxygen;
L$^1$ is tricyclohexylphosphine;
L$^2$ is a SIMes or SIPr ligand:

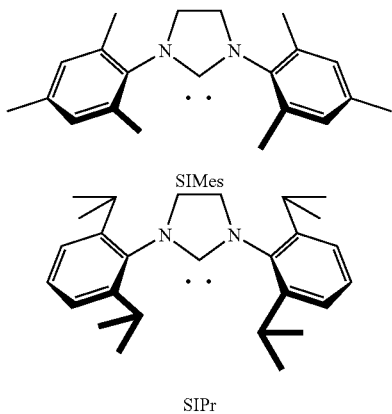

SIMes

SIPr

The invention is related also to use of the complexes of the general formula 1, wherein all substituents are as defined in claim 1, as (pre)catalysts in the metathesis reactions.

Preferably, the complexes of the general formula 1 are used as (pre)catalysts in the reactions of ring-closing metathesis, cross metathesis, homometathesis, alkene-alkyne type metathesis; more preferably, the complexes of the general formula 1 are used as (pre)catalysts in the reaction of ring-opening metathetic polymerisation.

The invention concerns also a process for carrying out the metathesis reaction of olefins, wherein at least one olefin is contacted with a complex of the general formula 1 as a (pre) catalyst.

Preferably, the metathesis reaction is carried out in an organic solvent; more preferably, the organic solvent is dichloromethane, dichloroethane, toluene, ethyl acetate.

Preferably, the metathesis reaction is carried out without any solvent.

Preferably, the metathesis reaction is carried out in the presence of a chemical activator; more preferably, the chemical activator is a Brønsted or Lewis acid or a halo-derivative of alkane or silane; most preferably, the activator is hydrogen chloride, chlorotrimethylsilane or p-toluenesulphonic acid.

Preferably, the metathesis reaction is a ring-opening metathetic polymerisation of dicyclopentadiene.

Preferably, the (pre)catalyst of the general formula 1 is added in the solid form to dicyclopentadiene.

In one preferred embodiment, the polymerisation reaction is initiated by heating the mixture of dicyclopentadiene and the (pre)catalyst of the general formula 1 to a temperature of 30° C. or higher.

Preferably, the starting material contains at least 94 wt. % of dicyclopentadiene.

In the preferred process, the metathesis reaction is carried out at a temperature of from 20 to 120° C.

In the preferred process, the metathesis reaction is carried out in a period of from 1 minute to 24 hours.

Preferably, the metathesis reaction is carried out in the presence of an additive promoting formation of cross bonds.

In one preferred embodiment, the metathesis reaction is carried out using the amount of the (pre)catalyst equal to or less than 1000 ppm.

Throughout the description of the invention and patent claims, if ppm (parts per million) units are used with relation to amount of substance, these are on a weight basis.

Since the inventors do not wish to be bound by any particular mechanism of catalysis, the "(pre)catalyst" term is used to indicate that the complex according to the invention may be either the catalyst itself or a precursor of the active species being the actual catalyst.

The definitions of groups not defined below should have the broadest meanings known in the art.

The term "optionally substituted" means that one or more hydrogen atoms of the group in question have been replaced with the specified groups, provided that such a substitution results in formation of a stable compound.

The term "halo" or "halogen" represents an element selected from F, Cl, Br, I.

The term "alkyl" concerns a saturated, straight-chain or branched-chain hydrocarbon substituent having the specified number of carbon atoms. The non-limiting examples of alkyls are: methyl, ethyl, propyl, isopropyl, butyl, sec-butyl, tert-butyl, pentyl.

The term "alkoxy" concerns the alkyl substituent, as defined above, bound via an oxygen atom.

The term "perfluoroalkyl" represents the alkyl, as defined above, wherein all hydrogens have been replaced with halogen atoms, where the halogen atoms may be identical or different.

The term "cycloalkyl" concerns a saturated mono- or polycyclic hydrocarbon substituent having the specified number of carbon atoms. The non-limiting examples of a cycloalkyl substituent are cyclopropyl, cyclobutyl, cyclopentyl, cyclohexyl.

The term "alkenyl" concerns a non-cyclic, straight or branched hydrocarbon chain having the specified number of carbon atoms and containing at least one carbon-carbon double bond. The non-limiting examples of alkenyls are: vinyl, allyl, 1-butenyl, 2-butenyl.

The term "aryl" concerns an aromatic mono- or polycyclic hydrocarbon substituent having the specified number of carbon atoms. The non-limiting examples of aryl are: phenyl, mesityl, anthracenyl.

The term "heterocyclyl" concerns aromatic as well as non-aromatic cyclic substituents having the specified number of carbon atoms, wherein one or more carbon atoms have been replaced with a heteroatom such as nitrogen, phosphorus, sulphur, oxygen, provided that there are no two directly connected oxygen or sulphur atoms in the ring. Non-aromatic heterocyclyls can contain from 4 to 10 atoms in the ring, whereas aromatic heterocyclyls must have at least 5 atoms in the ring. The benzo-fused systems also belong to heterocyclyls. The non-limiting examples of non-aromatic heterocyclyls are: pyrrolidinyl, tetrahydrofuranyl, dihydrofuranyl, tetrahydrothienyl, tetrahydropyranyl, dihydropyranyl, tetrahydrothiopyranyl, piperidinyl, morpholinyl, thiomorpholinyl, 2-pyrrolinyl, indolinyl. The non-limiting examples of aromatic heterocyclyls are: pyridinyl, imidazolyl, pyrimidinyl, pyrazolyl, triazolyl, pyrazinyl, furyl, thienyl. The above-mentioned groups may be bound via a carbon atom or a nitrogen atom. For example, the substituent obtained by binding pyrrole may be either pyrrol-1-yl (N-bound) or pyrrol-3-yl (C-bound).

The term "neutral ligand" concerns a substituent having no electrical charge, capable of co-ordinating to a ruthenium atom. The non-limiting examples of such ligands are: N-heterocyclic carbene ligands, amines, imines, phosphines and oxides thereof, alkyl and aryl phosphites and phosphates, ethers, alkyl and aryl sulphides, co-ordinated hydrocarbons, haloalkanes and haloarenes. The term "neutral ligand" encompasses also N-heterocyclic compounds; their non-limiting examples are: pyridine, 4-(N,N-dimethylamino)pyridine (DMAP), 3-bromopyridine, piperidine, morpholine, pyridazine, pyrimidine, pyrazine, piperazine, 1,2,3-triazole, 1,3,4-triazole, 1,2,3-triazine and 1,2,4-triazine.

The neutral ligands $L^1$ and $L^2$ may be bound with the benzylidene ligand, as well as they may be bound together to form a bidentate ligand ($L^1$-$L^2$); moreover, the neutral ligands may be bound to an anionic ligand X to form multidentate ligands.

The term "anionic ligand" concerns the substituent capable to co-ordination with a metal centre, bearing an electrical charge capable to compensate the charge of the metal centre, wherein such a compensation may be complete or partial. The non-limiting examples of anionic ligands are: fluoride, chloride, bromide or iodide anions, carboxylic acid anions, alcohol and phenol anions, thiol and thiophenol anions, (organo)sulphuric and (organo)phosphoric acid anions as well as anions of esters thereof. The anionic ligand (X) and the neutral ligands ($L^1$, $L^2$) may be bound together, resulting in formation of multidentate ligands. The non-limiting examples of multidentate ligands are: a bidentate ligand ($X^1$-$L^1$), a tridentate ligand ($X^1$-$L^1$-$L^2$). The non-limiting examples of such ligands are: anion of 2-hydroxyacetophenone, anion of acetylacetone.

The term "carbene" concerns a molecule containing a neutral carbon atom having the valence number of 2 and two non-paired valence electrons. The term "carbene" encompasses also carbene analogues, wherein the carbon atom is replaced with another chemical element such as: boron, silicon, nitrogen, phosphorus, sulphur. The term "carbene" relates particularly to N-heterocyclic carbene (NHC) ligands. The non-limiting examples of the NHC ligands are:

2c

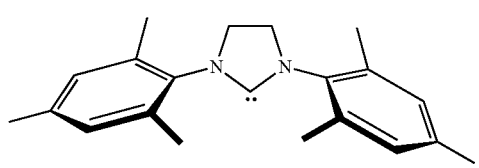

2d

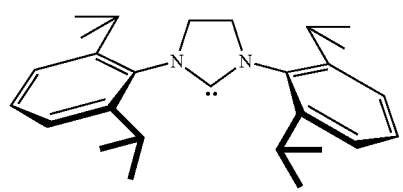

2e

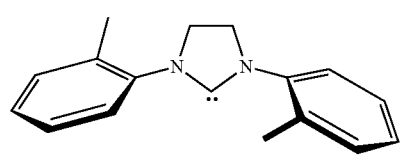

2f

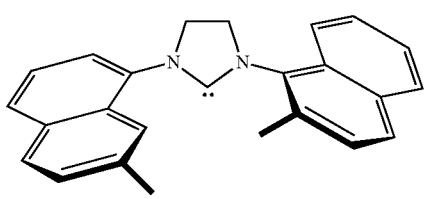

-continued

2g

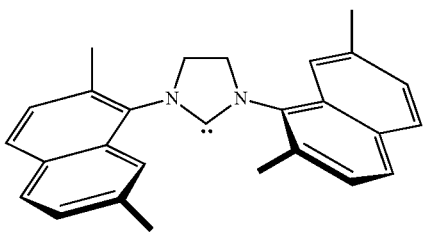

2h

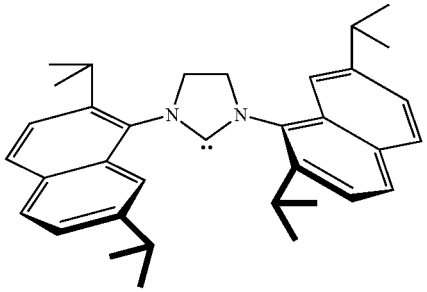

The non-limiting examples of preferred agents promoting formation of cross bonds are tert-butyl peroxide, di-tert-butyl peroxide, and also mixtures thereof.

EXAMPLES OF PREPARATION OF THE CATALYSTS

Example 1

Synthesis of the Complex 1a According to the Invention

The commercially available complex G' (200 mg, 0.24 mmol) was placed in a flask, and methylene chloride (15 ml) was added. This was followed by adding the compound of the formula:

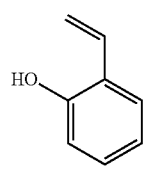

(58 mg, 0.48 mmol) and tricyclohexylphosphine (0.136 mg, 0.49 mmol). The resulting solution was stirred at a temperature of 40° C. for 30 minutes. The reaction mixture was cooled and introduced at the top of a chromatographic column packed with silica gel. The column was eluted using a solution of ethyl acetate-cyclohexane (0-10 vol. %), and a green-coloured fraction was collected. After evaporating the solvents, the complex 1a was obtained as a green solid (126 mg, 65% yield).

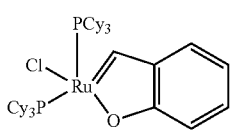

1a $^1$H NMR (300 MHz, CD$_2$Cl$_2$) δ ppm: 16.60 (s, 1H), 7.20 (dd, J=1.8 Hz, J=7.8 Hz, 1H), 7.14-7.09 (m, 1H), 6.90 (d, J=8.4 Hz, 1H), 6.47-6.42 (m, 1H), 2.02-0.85 (m, 66H). $^{13}$C NMR: (125 MHz, CD$_2$Cl$_2$) δ ppm: 279.34, 181.48, 149.47, 131.29, 122.44, 117.26, 113.05, 32.30, 29.93, 29.65, 29.43, 28.27, 27.89, 26.87, 23.11, 14.28. $^{31}$P NMR (124.5 MHz, CD$_2$Cl$_2$) δ ppm: 36.5.

Example 2

Synthesis of the Complex 2 According to the Invention

The commercially available complex G' (200 mg, 0.24 mmol) was placed in a flask, and dry, deoxygenated methylene chloride (6 ml) was added. This was followed by adding the compound of the formula:

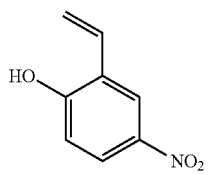

(80 mg, 0.48 mmol) and tricyclohexylphosphine (136 mg, 0.49 mmol). The resulting solution was stirred at room temperature for 24 hours. The reaction mixture was introduced at the top of a chromatographic column packed with silica gel (eluent: ethyl acetate/cyclohexane, 0 to 10 vol. %). After evaporating the solvents, the complex 2 was obtained as a brown solid (144 mg, 70% yield).

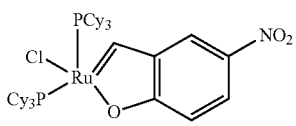

2

$^1$H NMR (500 MHz, CD$_2$Cl$_2$) δ ppm: 17.05 (s, 1H), 8.21 (d, J=2.7 Hz, 1H), 8.00 (dd, J=9.3, 2.7 Hz, 1H), 6.83 (d, J=9.3 Hz, 1H), 1.97-0.77 (m, 66H).
$^{13}$C NMR: (125 MHz, CD$_2$Cl$_2$) δ ppm: 280.71, 185.31, 147.04, 135.13, 126.50, 118.18, 116.07, 35.79, 35.31, 32.53, 32.45, 32.38, 29.82, 29.52, 28.16, 28.12, 28.08, 27.77, 27.73, 27.69, 27.32, 27.28, 27.22, 26.68, 26.55.

Example 3

Synthesis of the Complex 3 According to the Invention

The commercially available complex G (200 mg, 0.24 mmol) was placed in a flask, to which methylene chloride was added (6 ml). This was followed by adding the compound of the formula:

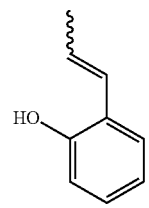

(63 mg, 0.47 mmol) and tricyclohexylphosphine (132 mg, 0.47 mmol). The resulting solution was stirred at a temperature of 40° C. for 5 hours. The reaction mixture was introduced at the top of a chromatographic column packed with silica gel (eluent: ethyl acetate/cyclohexane, 0 to 10 vol. %). After evaporating the solvents, the complex 3 was obtained as a green solid (140 mg, 72% yield).

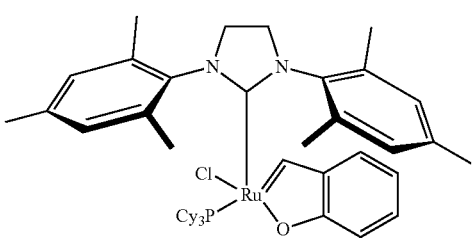

3

$^1$H NMR (500 MHz, CD$_2$Cl$_2$) δ ppm: 15.85 (s, 1H), 7.07 (s, 1H), 7.00-6.96 (m, 3H), 6.66 (d, J=8.4 Hz, 1H), 6.44 (dd, J=7.7, 1.4 Hz, 1H), 6.24 (s, 1H), 6.20 (t, J=7.2 Hz, 1H), 4.01-3.96 (m, 1H), 3.83-3.70 (m, 2H), 3.64-3.59 (m, 1H), 2.63 (s, 3H), 2.54 (s, 3H), 2.50 (s, 3H), 2.35 (s, 3H), 2.27 (s, 3H), 1.66-1.50 (m, 13H), 1.29 (s, 3H), 1.11-0.70 (m, 20H). $^{13}$C NMR: (125 MHz, CD$_2$Cl$_2$) δ ppm: 281.36, 222.21, 221.66, 180.31, 148.30, 139.54, 139.17, 138.78, 137.63, 137.32, 136.98, 134.69, 130.23, 130.05, 129.70, 129.00, 122.38, 116.17, 111.26, 32.52, 32.39, 29.45, 28.92, 28.23, 28.15, 28.12, 28.04, 27.34, 27.03, 21.33, 21.14, 19.40, 18.92, 18.66, 16.76. $^{31}$P NMR (124.5 MHz, CDCl$_3$) δ ppm: 29.11.

Example 4

Synthesis of the Complex 3 According to the Invention

The commercially available complex G (1.0 g, 1.18 mmol) was placed in a flask, to which methylene chloride was added (24 ml). This was followed by adding the compound of the formula:

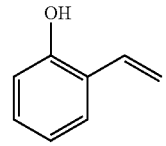

(141 mg, 1.17 mmol) and tricyclohexylphosphine (330 mg, 1.18 mmol). The resulting solution was stirred at a temperature of 40° C. for 5 hours. The reaction mixture was introduced at the top of a chromatographic column packed with silica gel (eluent: ethyl acetate/cyclohexane, 0 to 10 vol. %).

After evaporating the solvents, the complex 3 was obtained as a green solid (797 mg, 82% yield). The NMR data are consistent with Example 3.

Example 5

Synthesis of the Complex 4 According to the Invention

The commercially available complex G (200 mg, 0.24 mmol) was placed in a flask, to which methylene chloride was added (6 ml). This was followed by adding the compound of the formula:

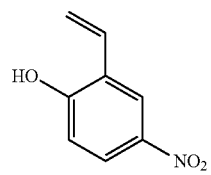

(78 mg, 0.47 mmol) and tricyclohexylphosphine (132 mg, 0.47 mmol). The resulting solution was stirred at a temperature of 40° C. for 1 hour. The reaction mixture was introduced at the top of a chromatographic column packed with silica gel (eluent: ethyl acetate/cyclohexane, 0 to 10 vol. %). After evaporating the solvents, the complex 4 was obtained as a brown solid (104 mg, 50% yield).

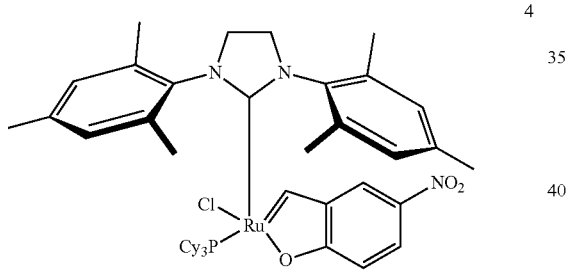

4

$^1$H NMR (500 MHz, CD$_2$Cl$_2$) δ ppm: 16.42 (s, 1H), 8.00 (dd, J=9.3, 2.7 Hz, 1H), 7.53 (d, J=2.7 Hz, 1H), 7.12 (s, 1H), 7.06 (s, 2H), 6.69 (d, J=9.3 Hz, 1H), 6.22 (s, 1H), 4.07-4.03 (m, 1H), 3.88-3.77 (m, 2H), 3.73-3.67 (m, 1H), 2.64 (s, 3H), 2.56 (s, 3H), 2.51 (s, 3H), 2.39 (s, 3H), 2.27 (s, 3H), 1.64-1.50 (m, 13H), 1.46 (m, 3H), 1.12-0.75 (m, 20H). $^{13}$C NMR: (125 MHz, CD$_2$Cl$_2$) δ ppm: 282.23 (d), 220.27, 219.73, 184.63 (d), 145.82, 139.23 (d), 139.08, 138.89, 137.46, 136.76, 136.69, 134.24, 134.00, 130.55, 130.36, 129.41 (d), 125.78, 117.59, 115.27, 52.14 (d), 51.63 (d), 34.52, 32.77, 32.64, 29.40, 28.91, 28.00 (m), 26.90 (d), 22.73, 21.34, 21.01, 19.41, 18.63, 18.53, 17.10, 14.21.

Example 6

Synthesis of the Complex 5 According to the Invention

Using the protective argon atmosphere, the solid carbene complex 4 (100 mg, 0.115 mmol) was placed in a Schlenk flask, this was followed by adding anhydrous, deoxygenated methylene chloride (7 ml) and anhydrous pyridine (93 µl, 1.15 mmol). The resulting solution was stirred at a temperature of 40° C. for 24 hours. The reaction mixture was introduced at the top of a chromatographic column packed with silica gel. Since that moment, all subsequent operations were carried out in the air, with no need for using the protective argon atmosphere. The column was eluted using a solution of ethyl acetate-cyclohexane (0 to 10 vol. %). After evaporating the solvents, the complex 5 was obtained as a brown solid (42 mg, 54% yield).

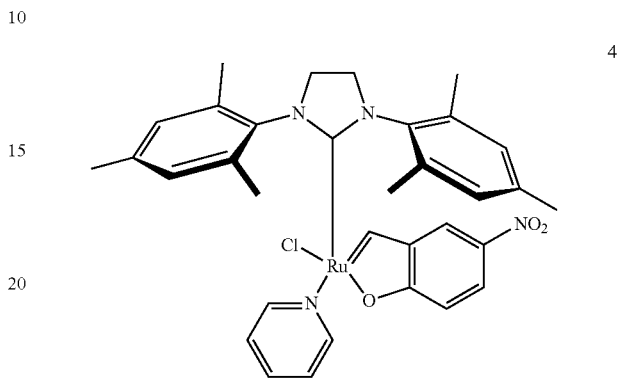

4

$^1$H NMR (500 MHz, CD$_2$Cl$_2$) δ ppm: 16.82 (s, 1H), 8.04 (dd, J=9.3, 2.7 Hz, 2H), 7.58 (s, 2H), 7.51 (m, 1H), 7.13 (d, J=4.5 Hz, 4H), 6.96 (s, 1H), 6.71 (d, J=9.3 Hz, 2H), 3.95-3.90 (m, 4H), 2.49 (s, 9H), 2.25 (s, 9H). $^{13}$C NMR: (125 MHz, CD$_2$Cl$_2$) δ ppm: 284.48, 219.30, 184.74, 150.09, 134.63, 126.06, 123.98, 117.54, 115.74, 35.90, 27.16, 25.79, 24.42, 20.93, 18.36.

Example 7

Synthesis of the Complex 6 According to the Invention

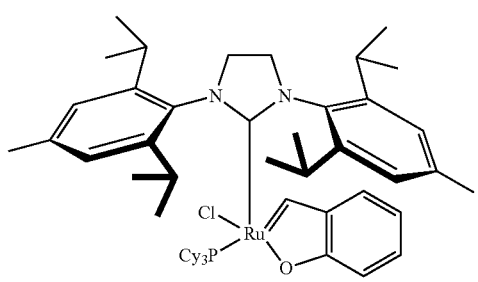

6

The complex 6 was prepared according to the method described for the complex 3 (in Example 4), to obtain the product as a green solid in 70% yield.

$^1$H NMR (500 MHz, CD$_2$Cl$_2$) δ ppm: 15.67 (s, 1H), 7.41 (d, J=4.7 Hz, 2H), 7.38-7.34 (m, 2H), 7.28 (t, J=7.7 Hz, 1H), 6.90-6.87 (m, 1H), 6.67-6.63 (m, 2H), 6.31 (dd, J=1.5 Hz, J=7.5 Hz, 1H), 6.07 (t, J=7.5 Hz, 1H), 4.15-4.04 (m, 2H), 3.94-3.88 (m, 2H), 3.80-3.77 (m, 1H), 3.75-3.68 (m, 2H), 2.33 (heptet, J=7.0 Hz, 1H), 1.66-1.45 (m, 21H), 1.41-1.38 (m, 3H), 1.29 (d, J=7.0 Hz, 3H), 1.21 (d, J=7.0 Hz, 3H), 1.08 (d, J=7.0 Hz, 3H), 1.04-0.98 (m, 9H), 0.91 (d, J=7.0 Hz, 3H), 0.89-0.85 (m, 6H), 0.79-0.70 (m, 3H), 0.32 (d, J=7.0 Hz, 3H). $^{13}$C NMR: (125 MHz, CD$_2$Cl$_2$) δ ppm: 281.27, 224.79, 224.23, 180.87, 152.55, 149.53, 149.20, 148.87, 147.47, 138.38, 136.02, 130.06, 129.05, 125.44, 124.45, 124.29, 124.05, 122.74, 117.33, 111.44, 31.87, 31.74, 29.70, 29.03, 28.23, 27.34, 26.89, 24.26, 23.84, 23.03, 21.35.

In the following examples, the specific reaction conditions used are presented in the corresponding tables, as well as the appropriate complexes used as (pre)catalysts.

Example 8

Ring-Closing Metathesis

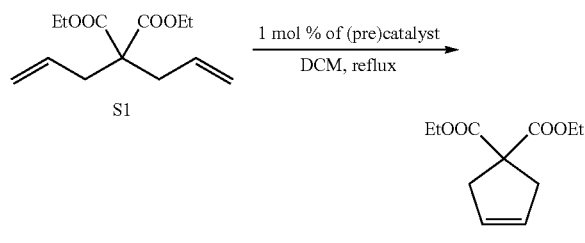

The diene S1 (100 mg, 0.416 mmol) was placed in a Schlenk flask, and this was followed by adding dichloromethane (DCM) (4 ml) and chlorotrimethylsilane (10 mol %) [in the case of experiments No. 3 and 13, no chemical activator was added], followed by the (pre)catalyst (1 mol %). The contents of the flask was stirred at a temperature of 40° C. The raw reaction mixture, to which vinyl-ethyl ether was added (in order to quench the reaction), was analysed using a gas chromatograph. The results are presented in the table below.

| No. | (Pre)catalyst | Activator | Time [h] | P1[a] [%] |
|---|---|---|---|---|
| 1 | 1 | TMSCl | 2 | 25 |
| 2 | 2 | TMSCl | 6 | 52 |
| 3 | 3 | none | 2 | 11 |
| 4 | 3 | HCl | 1 | 74 |
| 5 | 3 | TMSCl | 1 | 87 |
| 6 | 3 | TMSCl | 6 | 87 |
| 7 | 3 | $C_2Cl_4$ | 2 | 74 |
| 8 | 3 | $CF_3COOH$ | 2 | 15 |
| 9 | 4 | TMSCl | 1 | 47 |
| 10 | 4 | TMSCl | 6 | 96 |
| 11 | 5 | TMSCl | 1.5 | 67 |
| 12 | 6 | TMSCl | 0.3 | >99 |
| 13 | H | none | 2 | 99 |

[a] yield calculated based on results of the GC analysis GC

Example 9

Ring-Closing Metathesis

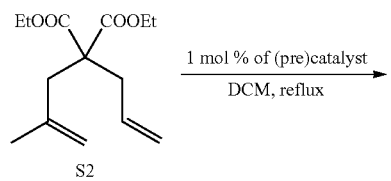

The diene S2 (100 mg, 0.393 mmol) was placed in a Schlenk flask, and this was followed by adding DCM (4 ml) and chlorotrimethylsilane (10 mol %) [in the case of experiments No. 3 and 4, no chemical activator was added], followed by the (pre)catalyst (1 mol %). The contents of the flask was stirred at a temperature of 40° C. The raw reaction mixture, to which vinyl-ethyl ether was added (in order to quench the reaction), was analysed using a gas chromatograph. The results are presented in the table below.

| No. | (Pre)catalyst | Activator | Time [h] | P1[a] [%] |
|---|---|---|---|---|
| 1 | 3 | TMSCl | 2 | 63 |
| 2 | 6 | TMSCl | 1.5 | 98 |
| 3 | 6 | none | 1.5 | 16 |
| 4 | H | none | 2 | 97 |

[a] yield calculated based on results of the GC analysis GC

Example 10

Cross Metathesis

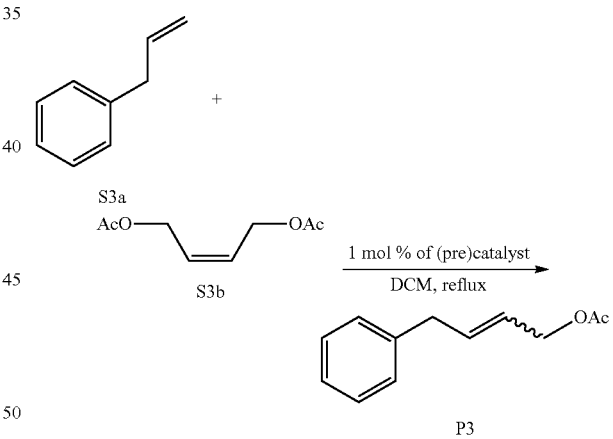

A solution of the substrates S3a (178 mg, 1.48 mmol) and S3b (510 mg, 2.96 mmol) in DCM (14 ml) was placed in a Schlenk flask, this was followed by adding chlorotrimethylsilane (10 mol %), followed by the (pre)catalyst (1 mol %). The contents of the flask was stirred at a temperature of 40° C. for 24 hours. The reaction progress was monitored by gas chromatography. The product P3 was isolated using column chromatography. The results are presented in the table below:

| No. | (Pre)catalyst | Activator | Time [h] | P3 [%] |
|---|---|---|---|---|
| 1 | 3 | TMSCl | 24 | 95 |
| 2 | 6 | TMSCl | 24 | 66 |

Example 11

Alkene-Alkyne Type Metathesis

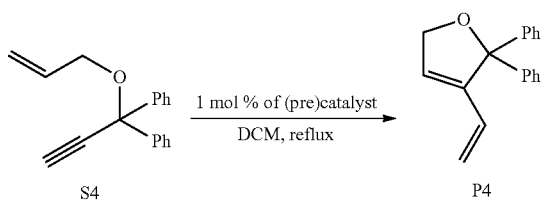

A solution of the substrate S4 (300 mg, 1.21 mmol) in DCM (12 ml) was placed in a Schlenk flask, this was followed by adding chlorotrimethylsilane (10 mol %) [in the case of experiment No. 4, no chemical activator was added], followed by the (pre)catalyst (1 mol %). The contents of the flask was stirred at a temperature of 40° C. The product P4 was isolated using column chromatography. The results are presented in the table below:

| No. | (Pre)catalyst | Activator | Time [h] | P3 [%] |
|---|---|---|---|---|
| 1 | 3 | TMSCl | 24 | 57 |
| 2 | 6 | TMSCl | 24 | 76 |
| 3 | 6 | HCl | 0.5 | 78 |
| 4 | 6 | none | 2 | 3[a] |

[a] yield calculated based on results of the GC analysis GC

Example 12

Ring-Opening Metathetic Polymerisation

Preparation of polydicyclopentadiene: Dicyclopentadiene (1 g, 7.56 mmol) was charged into the polymerisation vial, in the air, and, after melting, it was placed in an oil bath at a temperature of 28° C. Then appropriate amounts of the (pre) catalyst (as a solid in experiments 2, 3, 6-11, or as a solution in a minimum amount of dichloromethane) as well as of the chemical activator (4 equivalents with relation to the (pre) catalyst; no activator was added in the case of experiments 1-3) were added, and the vial was transferred to a bath at an appropriate temperature (as indicated in the table below) and kept for an appropriate period of time (as indicated in the table below). Then toluene was added to the vial and refluxed in order to wash out unreacted dicyclopentadiene. The insoluble polydicyclopentadiene, P5, was washed with toluene and dried under reduced pressure for 12 h. The results of the experiments are presented in the table below:

| No. | (Pre)catalyst (ppm) | Activator[a] | T [° C.] | t [min] | P5 [%] | Form of P5 |
|---|---|---|---|---|---|---|
| 1 | G (400) | none | 28 | 30 | >99 | hard solid |
| 2 | 3 (400) | none | 28 | 180 | none | — |
| 3 | 3 (400) | none | 28 | 960 | 90 | gel |
| 4 | 2 (6900) | TMSCl | 60 | 5 | >99 | hard solid |
| 5 | 2 (3400) | TMSCl | 60 | 10 | >99 | hard solid |
| 6 | 3 (500) | HCl | 40 | 1 | >99 | hard solid |
| 7 | 3 (250) | HCl | 40 | 15 | 97 | hard solid |
| 8 | 3 (200) | HCl | 80 | 10 | >99 | hard solid |
| 9 | 3 (150) | HCl | 80 | 30 | >99 | hard solid |
| 10 | 3 (100) | HCl | 80 | 120 | 97 | soft solid |
| 11 | 3 (50) | HCl | 80 | 120 | 75 | soft solid |
| 12 | 4 (200) | HCl | 80 | 10 | >99 | hard solid |
| 13 | 4 (200) | p-TsOH | 80 | 60 | 85 | gel |

[a] an appropriate amount was added, in the form of: pure TMSCl, 4M HCl in 1,4-dioxane, 1M p-TsOH in 1,4-dioxane.

Example 13

Ring-Opening Metathetic Polymerisation

Preparation of polydicyclopentadiene: Dicyclopentadiene (10 g, 76 mmol) was charged into the polymerisation vial, in the air, and, after melting, it was placed in an oil bath at a temperature of 28° C. Then the (pre)catalyst 4 (as a solution in a minimum amount of dichloromethane) was added and the vial was kept in a bath at a temperature of 28° C. for 24 h. No substrate conversion was observed (the vial contained liquid monomer only). Then HCl (4 equivalents with relation to the (pre)catalyst, solution in 1,4-dioxane) was added to the vial, and the vial was transferred to a bath at a temperature of 60° C. After 10 minutes, toluene was added to the vial and refluxed in order to wash out unreacted dicyclopentadiene. The insoluble polydicyclopentadiene (P5) was washed with toluene and dried under reduced pressure for 12 h. The reaction yield was >99%.

As shown in Examples 8-13, the complexes of the general formula 1 according to the invention, promote the olefin metathesis reactions effectively, following chemical activation. In particular, the complexes 3 and 4 demonstrate a very high effectiveness in the ring-opening polymerisation (ROMP) of dicyclopentadiene. The initiation of the polymerisation reaction may be controlled to a very high degree due to delayed initiation characterising the complexes of the general formula 1. The state of the art complexes of the formulae D and D' exhibit similar properties and effectiveness, as results from the literature data. However, these complexes are synthesized by using the appropriate thallium derivatives what presents the health concerns (thallium compounds used in the synthesis are very toxic) as well as lengthens and complicates the synthesis of such complexes. The properties of the complexes of the general formula 1 may be significantly altered by the choice of appropriate ligands. Besides, the high stability of the complexes of the general formula 1 allows for carrying out the polymerisation process in the presence of oxygen; because of that, there is no need for deoxygenating the commercially available dicyclopentadiene and also it is not necessary to use an inert gas atmosphere during the process itself. It is unexpectedly found that the course of the polymerisation reaction (the form of the polymer) may be controlled by the choice of the activating agent. For example, using 200 ppm of the complex 4 makes it possible to obtain a hard solid polymer within 10 minutes, if hydrogen chloride is used for activation, whereas using p-toluenesulphonic acid (p-TsOH) allows for obtaining the polymer in the gel form. An additional advantage of some complexes of the general formula 1 is their excellent solubility in pure, liquid DCPD. This fact eliminates the need for prior dissolving the (pre) catalyst in an organic solvent. As shown in Examples 8, 12 and 13, the complexes of the general formula 1 containing the electron-acceptor group initiate the metathesis reactions slower than the unsubstituted complexes. Thus, this effect is reversed compared to the case of classic complexes of the Hoveyda-Grubbs type (H and I). As shown in Examples 12 and 13, this is of significance in the case of polymerisation of DCPD. A mixture of the complex 4 and the monomer may be prepared even 24 h before the planned starting of mould polymerisation, whereas the complex 3 causes partial polymerisation of the monomer in this time.

The invention claimed is:

1. A complex of the general formula 1:

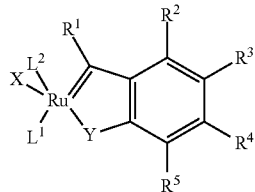

wherein,

X is an anionic ligand;
Y is oxygen;
$L^1$ is a neutral ligand other than an N-heterocyclic carbene ligand;
$L^2$ is an N-heterocyclic carbene ligand;
$R^1$ is hydrogen, —$C_{1-20}$ alkyl, —$C_{2-20}$ alkenyl, —$C_{2-20}$ alkynyl or —$C_{5-10}$ aryl; and
$R^2$, $R^3$, $R^4$ and $R^5$ are independently hydrogen, halo, $C_1$-$C_{16}$ alkyl, $C_1$-$C_{16}$ alkoxy, $C_1$-$C_{16}$ perfluoroalkyl, $C_3$-$C_7$ cycloalkyl, $C_2$-$C_{16}$ alkenyl, $C_5$-$C_{14}$ aryl, $C_5$-$C_{14}$ perfluoroaryl, $C_3$-$C_{12}$ heterocyclyl, —$OR^6$, —$NO_2$, —COOH, —$COOR^6$, —$CONR^6R^7$, —$SO_2NR^6R^7$, —$SO_2R^6$, —CHO, —$COR^6$, wherein $R^6$ and $R^7$ are independently $C_1$-$C_6$ alkyl, $C_1$-$C_6$ perfluoroalkyl, $C_5$-$C_{14}$ aryl, $C_5$-$C_{14}$ perfluoroaryl; or $R^2$, $R^3$, $R^4$ and $R^5$ may be optionally joined together to form a substituted or unsubstituted, fused carbocyclic $C_{4-8}$ ring, or a substituted or unsubstituted, fused aromatic ring.

2. A complex according to claim 1, wherein,
X is halo, —$OR^8$, —$O(C=O)R^8$, or —$O(SO_2)R^8$, wherein $R^8$ is $C_1$-$C_{12}$ alkyl, $C_3$-$C_{12}$ cycloalkyl, $C_5$-$C_{14}$ aryl, that is optionally substituted with at least one $C_1$-$C_6$ alkyl, $C_1$-$C_6$ perhaloalkyl, $C_1$-$C_6$ alkoxy or halo;
$L^1$ is of the formula $PR^9(R^{10})(R^{11})$, wherein $R^9$, $R^{10}$ and $R^{11}$ are independently $C_{1-12}$ alkyl, $C_{1-12}$ alkoxy, $C_{3-12}$ cycloalkyl, $C_{5-14}$ aryl, $C_{5-14}$ aryloxy, $C_{5-12}$ heterocyclyl; and two substituents from among $R^9$, $R^{10}$ and $R^{11}$ may additionally join together to form a cyclic system; or $L^1$ is an N-heterocyclic compound.

3. A complex according to claim 1 wherein
X is chloro;
$R^1$ is hydrogen;
$R^2$, $R^3$, $R^4$ and $R^5$ are independently hydrogen or nitro;
Y is oxygen;
$L^1$ is tricyclohexylphosphine, triphenylphosphine, pyridine or 3-bromopyridine; and
$L^2$ is a ligand of the formula 2a or 2b:

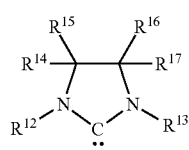

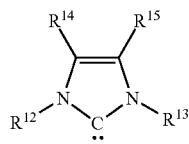

where:
$R^{12}$, $R^{13}$ are independently $C_1$-$C_{12}$ alkyl, $C_3$-$C_{12}$ cycloalkyl, $C_2$-$C_{12}$ alkenyl, $C_5$-$C_{14}$ aryl, optionally substituted with at least one of $C_1$-$C_6$ alkyl, $C_1$-$C_6$ perhaloalkyl, $C_1$-$C_6$ alkoxy or halo;
$R^{14}$, $R^{15}$, $R^{16}$, $R^{17}$ are independently hydrogen, $C_1$-$C_{12}$ alkyl, $C_3$-$C_{12}$ cycloalkyl, $C_2$-$C_{12}$ alkenyl, $C_5$-$C_{14}$ aryl, optionally substituted with at least one of $C_1$-$C_6$ alkyl, $C_1$-$C_6$ perhaloalkyl, $C_1$-$C_6$ alkoxy or halo, and $R^{14}$, $R^{15}$, $R^{16}$, $R^{17}$ may optionally join together to form a substituted or unsubstituted, fused carbocyclic ring $C_{4-8}$, or a substituted or unsubstituted, fused aromatic ring.

4. A complex according to claim 1, wherein,
X is chloro;
$R^1$ is hydrogen;
$R^2$, $R^3$, $R^4$ and $R^5$ are independently hydrogen or nitro;
Y is oxygen;
$L^1$ is tricyclohexylphosphine; and
$L^2$ is a SIMes or SIPr ligand:

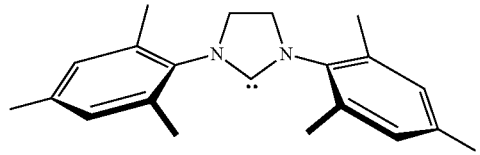

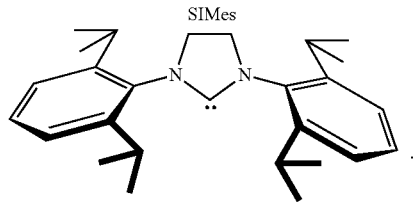

5. A process for carrying out a metathesis reaction of olefins, comprising contacting at least one olefin with the complex of claim 1 as a (pre)catalyst.

6. The process according to claim 5, wherein the metathesis reaction is carried out in an organic solvent.

7. The process according to claim 6, wherein the organic solvent is dichloromethane, dichloroethane, toluene, ethyl acetate.

8. The process according to claim 5, wherein the metathesis reaction is carried out without any solvent.

9. The process according to claim 5, wherein the metathesis reaction is carried out in the presence of a chemical activator.

10. The process according to claim 9, wherein the chemical activator is a Brønsted or Lewis acid or a halo-derivative of alkane or silane.

11. The process according to claim 10, wherein the activator is hydrogen chloride, chlorotrimethylsilane or p-toluenesulphonic acid.

12. The process according to claim 5, wherein the metathesis reaction is a ring-opening metathetic polymerisation of dicyclopentadiene.

13. The process according to claim 12, wherein the (pre)catalyst of the general formula 1 is added in the solid form to dicyclopentadiene.

14. The process according to claim 12, wherein the polymerisation reaction is initiated by heating the mixture of dicyclopentadiene and the (pre)catalyst of the general formula 1 to a temperature of 30° C. or higher.

15. The process according to claim 12, wherein the starting material contains of at least 94 wt. % of dicyclopentadiene.

16. The process according to claim 5, wherein the metathesis reaction is carried out at a temperature of from 20 to 120° C.

17. The process according to claim 5, wherein the metathesis reaction is carried out in a period of from 1 minute to 24 hours.

18. The process according to claim 5, wherein the metathesis reaction is carried out in the presence of an additive promoting formation of cross bonds.

19. The process according to claim 5, wherein the metathesis reaction is carried out using the amount of the (pre)catalyst equal to or less than 1000 ppm.

* * * * *